(12) United States Patent
Yajima (10) Patent No.: US 10,088,638 B2
(45) Date of Patent: Oct. 2, 2018

(54) OPTICAL FIBER CONNECTION MECHANISM AND OPTICAL FIBER CONNECTION METHOD

(71) Applicant: OLYMPUS CORPORATION, Tokyo (JP)

(72) Inventor: Hiroyoshi Yajima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/602,832

(22) Filed: May 23, 2017

(65) Prior Publication Data

US 2017/0254964 A1    Sep. 7, 2017

Related U.S. Application Data

(63) Continuation of application No. PCT/JP2014/005918, filed on Nov. 26, 2014.

(51) Int. Cl.
*G02B 6/38* (2006.01)
*A61B 1/00* (2006.01)
(Continued)

(52) U.S. Cl.
CPC ........ *G02B 6/3877* (2013.01); *A61B 1/00126* (2013.01); *G02B 6/0008* (2013.01);
(Continued)

(58) Field of Classification Search
CPC .. G02B 6/3825; G02B 6/3869; G02B 6/3875; G02B 6/3877; A61B 1/00126
See application file for complete search history.

(56) References Cited

U.S. PATENT DOCUMENTS 4,414,608 A * 11/1983 Furihata ............. A61B 1/00117
352/198
5,428,703 A * 6/1995 Lee ....................... G02B 6/3887
385/60
(Continued)

FOREIGN PATENT DOCUMENTS

JP    H02-115809 A    4/1990
JP    H03-148610 A    6/1991
(Continued)

OTHER PUBLICATIONS

International Search Report dated Feb. 17, 2015 issued in PCT/JP2014/005918.
(Continued)

*Primary Examiner* — Rhonda Peace
(74) *Attorney, Agent, or Firm* — Scully, Scott, Murphy & Presser, P.C.

(57) ABSTRACT

An optical fiber connection mechanism includes a pair of connectors and a split sleeve that are used in an endoscope. The connectors include respective ferrules, an end of a single-mode optical fiber and a collimator lens is mounted in each ferrule, and the collimator lens is disposed at the tip of the single-mode optical fiber. The optical fiber connection mechanism is configured so that when the ferrules are inserted into ends of the split sleeve, the collimator lenses face each other with a gap therebetween and the single-mode optical fibers are optically connected to each other. The ferrules are loosely fit in the corresponding connectors to be displaceable within a predetermined range in the direction along the optical axis of the single-mode optical fibers.

11 Claims, 12 Drawing Sheets

(51) Int. Cl.
*F21V 8/00* (2006.01)
*G02B 23/24* (2006.01)

(52) U.S. Cl.
CPC ......... *G02B 6/3831* (2013.01); *G02B 6/3849* (2013.01); *G02B 6/3853* (2013.01); *G02B 6/3878* (2013.01); *G02B 23/2469* (2013.01)

(56) References Cited

U.S. PATENT DOCUMENTS

| | | | | |
|---|---|---|---|---|
| 6,048,102 | A * | 4/2000 | Fukushima | G02B 6/3821 385/140 |
| 6,501,900 | B1 * | 12/2002 | Aloisio, Jr. | G02B 6/266 385/140 |
| 7,236,669 | B2 * | 6/2007 | Asano | G02B 6/3825 385/50 |
| 7,986,861 | B2 * | 7/2011 | Shimotsu | G02B 6/32 385/115 |
| 8,727,635 | B2 * | 5/2014 | Livingston | G02B 6/3825 385/50 |
| 9,025,917 | B2 * | 5/2015 | Aoki | G02B 6/327 385/33 |
| 9,658,405 | B2 * | 5/2017 | Philippe | G02B 6/3821 |
| 2007/0088198 | A1 | 4/2007 | Koitabashi | A61B 1/07 600/136 |
| 2010/0027943 | A1 * | 2/2010 | Armani | B01L 3/502715 385/74 |
| 2016/0324402 | A1 * | 11/2016 | Yajima | G02B 6/3874 |
| 2017/0035275 | A1 * | 2/2017 | Yajima | G02B 6/36 |
| 2017/0245745 | A1 * | 8/2017 | Ohara | A61B 1/0661 |
| 2017/0254964 | A1 * | 9/2017 | Yajima | G02B 6/3877 |
| 2017/0261696 | A1 * | 9/2017 | Compton | G02B 6/3869 |
| 2017/0261698 | A1 * | 9/2017 | Compton | G02B 6/3874 |

FOREIGN PATENT DOCUMENTS

| | | |
|---|---|---|
| JP | 2005-003871 A | 1/2005 |
| JP | 2012-143414 A | 8/2012 |
| JP | 2014-002256 A | 1/2014 |
| WO | WO 2012/029442 A1 | 3/2012 |
| WO | WO 2014/115360 A1 | 7/2014 |

OTHER PUBLICATIONS

Inaba, F., et al. "Introduction to Optoelectronics", Ohmsha, Dec. 1991, p. 133, 2nd revised edition, with partial English translation.
Hatori, M., et al. "Optical Communication Engineering (2)", Corona, Jul. 1998, pp. 118-119 and 126-128, with partial English translation.
"The Current State and Future of Optical Communication Technology" edited by the Telecommunications Technology Council, Gyosei, Mar. 1987, p. 203, with partial English translation. Retrieved from "Electrical Communication Laboratories Technical Journal" vol. 32, No. 3, 1983.

* cited by examiner

OPTICAL FIBER CONNECTION MECHANISM AND OPTICAL FIBER CONNECTION METHOD

CROSS-REFERENCE TO RELATED APPLICATION

The present application is a Continuing Application based on International Application PCT/JP2014/005918 filed on Nov. 26, 2014, the entire disclosure of which is incorporated herein by reference.

TECHNICAL FIELD

The present disclosure relates to an optical fiber connection mechanism and an optical fiber connection method.

BACKGROUND

In recent years, in the field of endoscope apparatuses, a variety of endoscopes have been developed, such as a laser scanning endoscope that drives the tip of a scope by vibration in a body cavity, irradiates laser light onto an examination site while scanning, detects the resulting reflected light and the like, and generates a 2D image; a confocal endoscope that obtains a clear, high-magnification and high-resolution image using a confocal technique; and an endoscope equipped with a laser light source used to generate white light with a fluorescent body and irradiate an examination site. In such apparatuses, the resolution depends on the spot diameter of the irradiation light. Therefore, in order to obtain high resolution, it is necessary to convey light from a laser light source using a single-mode optical fiber, rather than with a lamp light source and light guide bundle of an imager endoscope. Hence, the single-mode optical fiber needs to be repeatedly attached and detached between the housing and scope.

As connection methods for attachment and detachment of a single-mode optical fiber, standards such as FC, SC, ST, MU, and LC have been established in the field of optical communication (for example, see NPL 1 to NPL 3). These connection methods are for using an optical adapter with a split sleeve to connect optical fiber connectors that each have a ferrule in which the tip of an optical fiber is embedded. The ferrule is a cylindrical member produced to be coaxial with the fiber that passes through the center thereof in order to connect two optical fibers. The split sleeve is a cylindrical member for aligning ferrules in series and abutting them together and has a slit in the longitudinal direction. In this method, the ferrules of the contacting optical fiber connectors are each inserted into the split sleeve from the sides of the optical fiber adapter, and the cores of the optical fibers are abutted and aligned inside the split sleeve. The split sleeve is formed from a hard material, such as zirconia, and serves to position and hold the ferrules together. In these standard connection methods, in order to ensure that the pair of ferrules are abutted against each other, a spring is provided in the housing of each connector to push the ferrule towards the connecting direction of the connector.

CITATION LIST

Non-patent Literature

NPL 1: "Introduction to Optoelectronics" (English translation of Japanese Title) by INABA Fumio, NAGAI Jun, and GOTO Kenya, $2^{nd}$ revised edition, Ohmsha, December 1991, p.133

NPL 2: "Optical Communication Engineering (2)" (English translation of Japanese Title) by HATORI Mitsutoshi, AOYAMA Yuki, and KOBAYASHI Ikutaro, Corona, July 1998, pp. 118-119, 126-128

NPL 3: "The Current State and Future of Optical Communication Technology" (English translation of Japanese Title) edited by the Telecommunications Technology Council, Gyosei, March 1987, p. 203

SUMMARY

An optical fiber connection mechanism according to the present disclosure includes:

a pair of connecting bodies and a tubular member that are used in an endoscope; wherein the connecting bodies comprise respective ferrules, an end of an optical fiber and a collimator lens is mounted in each ferrule, the collimator lens is disposed at a tip of the optical fiber, and when the respective ferrules of the connecting bodies are inserted into ends of the tubular member, the collimator lenses face each other with a gap therebetween and the optical fibers are optically connected to each other; and each ferrule is loosely fit in the corresponding connecting body to be displaceable within a predetermined range in a direction along an optical axis of the optical fiber.

The ferrules may be loosely fit in the corresponding connecting bodies to be displaceable within a predetermined range in an in-plane direction orthogonal to the optical axis of the optical fibers.

The optical fiber connection mechanism may further include an intermediate connecting body disposed between the pair of connecting bodies, such that the intermediate connecting body has openings into which the connecting bodies are inserted, and a width of the gap is set by a connection surface between the intermediate connecting body and the connecting bodies.

The tubular member may be housed in one of the pair of connecting bodies.

Furthermore, the intermediate connecting body may include an openable and closable door on at least one of the openings into which the pair of connecting bodies is inserted.

The connecting bodies may include an adjustment mechanism that contacts the intermediate connecting body to form the connection surface and that is capable of adjusting the width of the gap.

Furthermore, the optical fiber may be a single-mode optical fiber.

An optical fiber connection method according to the present disclosure is for connecting a pair of optical fibers for an endoscope, the connection method including:

preparing a pair of connecting bodies comprising respective ferrules, an end of an optical fiber and a collimator lens being mounted in each ferrule, the collimator lens being disposed at a tip of the optical fiber, and each ferrule being loosely fit in the corresponding connecting body to be displaceable within a predetermined range in a direction along an optical axis of the optical fiber; and optically connecting the pair of optical fibers by inserting the respective ferrules of the pair of connecting bodies into ends of a tubular member so that the collimator lenses face each other with a gap therebetween.

DETAILED DESCRIPTION

In a conventional connection method for attachment and detachment of a single-mode optical fiber, ferrules that contain optical fibers are abutted against each other. Therefore, if the ferrules are abutted together with dust adhered to the ferrule end faces, the connection efficiency might be reduced or a permanent reduction in connection efficiency might occur due to damage to the ferrule end faces. It thus becomes necessary to clean the ferrule end faces before connection with a specialized cleaner, which reduces the usability for the user of the endoscope.

Figure 12:
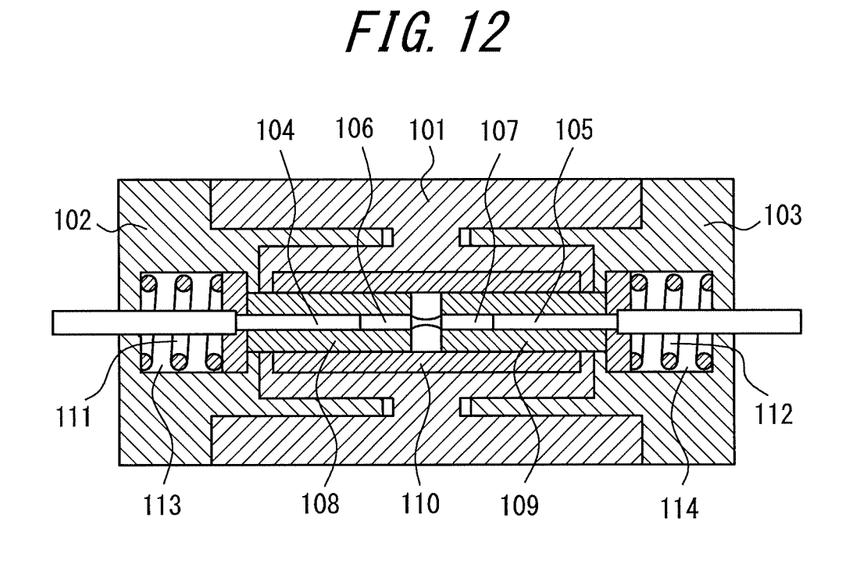
FIG. 12 is a longitudinal sectional view of a prototype adapter and prototype connectors that I produced.

I produced and examined a prototype of a connection mechanism to connect connectors 102 and 103 via an adapter 101, as illustrated in FIG. 12.

In this connection mechanism, fiber collimators in which collimator lenses 106, 107 are attached to the tips of fibers 104, 105 are mounted in ferrules 108 and 109, and the pair of ferrules 108 and 109 are connected inside a split sleeve 110 with a gap therebetween. By adopting this approach, the ferrules 108 and 109 are not abutted against each other, preventing damage to the ferrule end faces. Also, the beam diameter at the end face of the ferrules 108 and 109 is expanded by the collimator lenses 106 and 107, thereby reducing the effect of dust and making cleaning before each connection unnecessary.

When adopting a configuration with a gap provided between ferrules, however, the gap may expand upon repeated detachment and attachment, and the connection efficiency may change. Upon examining the cause, I discovered that the elongation of springs 111 and 112 that push the ferrules 108 and 109 when connecting the connectors 102 and 103 to the adapter 101 is not constant, which makes the gap change. Like the connector in a conventional technique, the springs 111 and 112 are provided to project the ferrules 108 and 109. Upon using springs with a large spring force in order to ensure elongation of the springs, I found that the ferrules 108 and 109 were not disposed in serial within the split sleeve, inclination occurred, and the optical connection efficiency degraded.

It would be helpful to provide an optical fiber connection mechanism and an optical fiber connection method for which the width of the gap between ferrules does not change even upon repeated attachment and detachment.

Embodiments of the present disclosure are described below with reference to the drawings.

Embodiment 1

Figure 1:
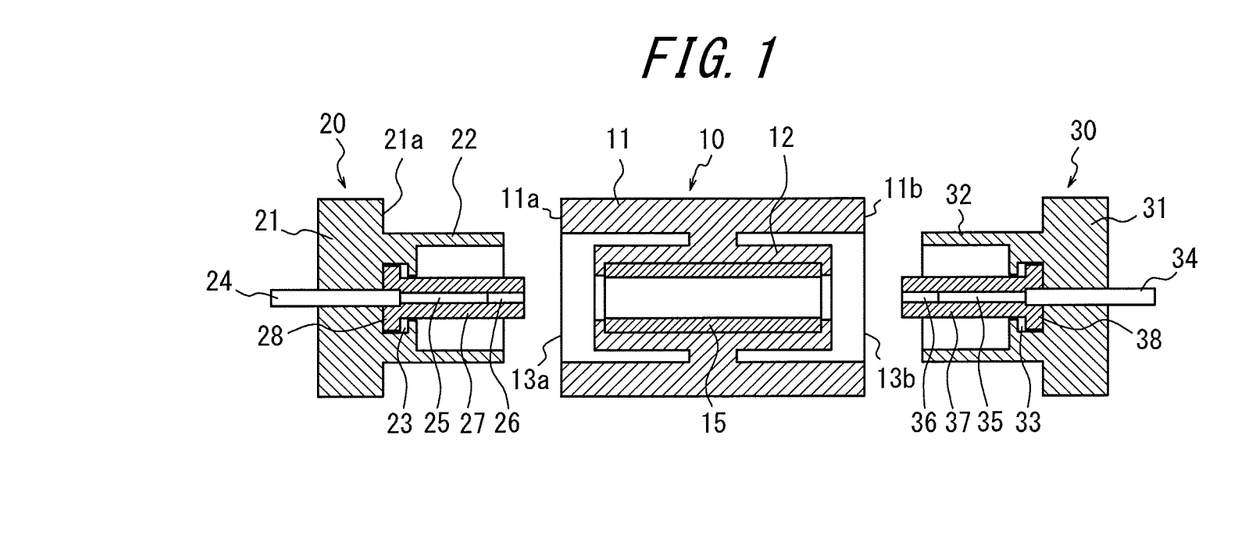
FIG. 1 is a longitudinal sectional view of an adapter and connectors according to Embodiment 1.
Figure 2:
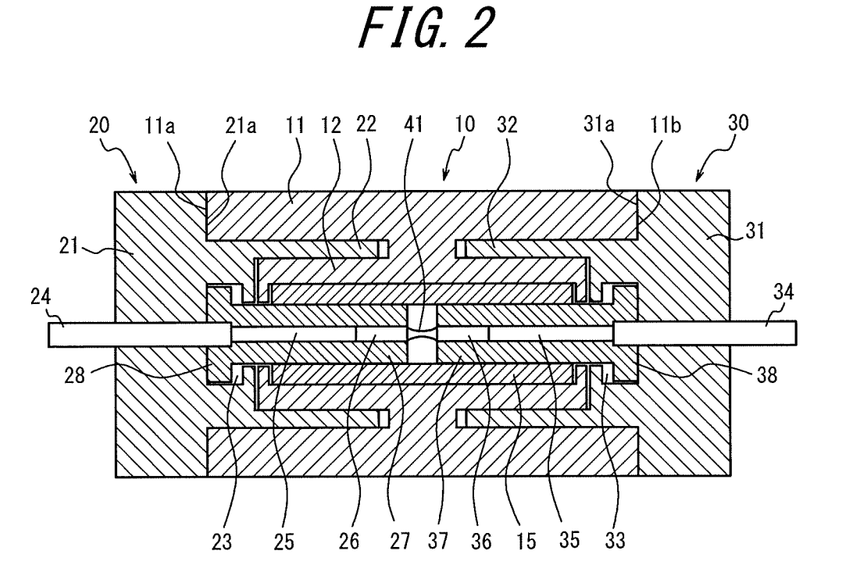
FIG. 2 is a longitudinal sectional view of the adapter and connectors in FIG. 1 in a coupled state.

FIG. 1 is a longitudinal sectional view of an adapter 10 and connectors 20 and 30 according to Embodiment 1. FIG. 2 is a longitudinal sectional view of the adapter 10 and the connectors 20 and 30 in FIG. 1 in a coupled state. The adapter 10 (intermediate connecting body) and the connectors 20 and 30 (connecting bodies) constitute a connecting mechanism for optical fibers. The adapter 10 and connectors 20 and 30 are for connecting optical fibers used in an endoscope apparatus and are used, for example, to connect single-mode optical fibers between the inside of a housing for a laser light source, or a housing to which a laser light source is connected, and the outside of the housing.

The adapter 10 includes an outer cylindrical portion 11 and an inner cylindrical portion 12, inside the outer cylindrical portion 11, that is shorter than the outer cylindrical portion 11. The outer cylindrical portion 11 and the inner cylindrical portion 12 are coupled near the center in the longitudinal direction, i.e. in a direction along the central axis of the outer cylindrical portion 11 and the inner cylindrical portion 12. As a result, there are openings 13a and 13b for housing the connectors 20 and 30 on the inside of the outer cylindrical portion 11. A tubular split sleeve 15 (tubular member) is provided inside the cavity of the inner cylindrical portion 12. The split sleeve 15 is a hollow tubular member that has a slit extending in the longitudinal direction and is formed from a hard ceramic or the like, such as zirconia. The inner circumferential surface at both ends of the inner cylindrical portion 12 projects inwards to prevent separation of the split sleeve 15.

The connectors 20 and 30 include respective connector housings 21 and 31, and the side of the connector housings 21 and 31 connected to the adapter 10 is respectively formed by cylindrical portions 22 and 32 that each have a cylindrical wall. The cylindrical portions 22 and 32 are formed to fit into the gaps between the inner cylindrical portion 12 and the outer cylindrical portion 11 of the adapter 10. The connector housings 21 and 31 respectively have roughly cylindrical cavities 23 and 33. Furthermore, the connectors 20 and 30 respectively include optical fiber cables 24 and 34 along the central axis and ferrules 27 and 37 in which are mounted the end of single-mode optical fibers 25 and 35 and collimator lenses 26 and 36. The collimator lenses 26 and 36 are disposed at the tip of the single-mode optical fibers 25 and 35. Hereinafter, the direction towards the collimator lenses 26 and 36 of the connectors 20 and 30 is referred to as the front, and the opposite direction is referred to as the back.

The ferrules 27 and 37 have a cylindrical shape with a chamfered tip, and the front of each protrudes from the respective connector housings 21 and 31. The diameter of the ferrules 27 and 37 is approximately equivalent to, or slightly larger than, the diameter of the inside of the split sleeve 15. The connecting portions for the optical fiber cables 24 and 34 positioned at the back end of the ferrules 27 and 37 are formed by flanges 28 and 38 expanded in the radial direction and are disposed in cavities 23 and 33 of the connectors 20 and 30. Furthermore, the outer periphery of the ferrules 27 and 37 is slidably supported, in a state with play, by the connector housings 21 and 31 between the portion protruding from the connector housings 21 and 31 and the flanges 28 and 38.

The flanges 28 and 38 are smaller than the cavities 23 and 33 inside the connector housings 21 and 31 in both the direction along the optical axis of the single-mode optical fibers 25 and 35 and the radial direction. As a result, the ferrules 27 and 37 are loosely fit in the corresponding connectors 20 and 30 to be displaceable within a predetermined range, allowed by the cavities 23 and 33, in the direction along the optical axis of the single-mode optical fibers 25 and 35 and a plane direction orthogonal to the optical axis. In this context, "displaceably" means freely displaceable, without being pushed in a particular direction by a spring or the like. A groove may be provided on the outer periphery of the flanges 28 and 38 in a direction along the optical axis of the single-mode optical fibers 25 and 35. By fitting a projection that projects inward from the connector housings 21 and 31 into this groove, rotation of the ferrule in a cross-section in the insertion direction can be restricted. By adopting this configuration, the connection efficiency can be further improved, and the efficiency of repeated attachment and detachment also becomes stable.

The collimator lens 26 housed at the tip of the ferrules 27 and 37 emits light propagating through the core of the single-mode optical fiber 25 into the cavity between the ferrule 27 and the ferrule 37 as parallel light with a large spot diameter or as convergent light. An emitted light beam 41 is incident on the collimator lens 36 with high efficiency and is guided into the single-mode optical fiber 35. As a result, the single-mode optical fiber 25 and the single-mode optical fiber 35 are connected to each other optically. A gradient index (GRIN) lens that has approximately the same diameter as the single-mode optical fibers 25 and 35 may be used as the collimator lenses 26 and 36. At this time, the collimator lenses 26 and 36 and the single-mode optical fibers 25 and 35 may be in contact, glass material of each lens may be fusion spliced, or the lenses may be held with a fixed gap therebetween. A non-reflective coating film may be provided on the opposite end face of the collimator lenses 26 and 36 from the optical fibers 25 and 35.

With the above-described configuration, when the connectors 20 and 30 are connected to the adapter 10, first, the axial line of the adapter 10 and the connectors 20 and 30 is aligned, and the ferrules 27 and 37 are fit in the split sleeve 15. Then, the cylindrical portions 22 and 32 of the connectors 20 and 30 are fit between the ends of the outer cylindrical portion 11 and the inner cylindrical portion 12 of the adapter 10 and pushed in. At this time, the flanges 28 and 38 of the ferrules 27 and 37 are positioned at the most receded position at the back of the cavities 23 and 33 by the frictional force acting between the ferrules 27 and 37 and the split sleeve 15. The adapter 10 is fixed relative to the connectors 20 and 30 at a position where a contact face 21a of the connector housings 21 and 31 of the connectors 20 and 30 abuts against a contact face 11 a of the outer cylindrical portion 11 of the adapter 10. As a result, the width of the gap is fixed. A non-illustrated latching mechanism is provided to fix the connectors 20 and 30 to the adapter 10.

When detaching the connectors 20 and 30 from the adapter 10, the latching mechanism is released, and the connectors 20 and 30 are withdrawn backward. As a result, the flanges 28 and 38 of the ferrules 27 and 37 move forward in the cavities 23 and 33 and are pressed by the front face of the cavities 23 and 33 to allow detachment from the split sleeve 15.

In this embodiment, a member such as the spring that pushes the ferrules 27 and 37 in a certain direction is not provided. Therefore, the gap between the two ferrules 27 and 37 is always stable. To optical fibers with a cladding diameter of ϕ125 µm that operate in a single mode with a wavelength of from 400 nm to 699 nm, I fusion spliced GRIN lenses with the same outer diameter as the cladding diameter, mounted the optical fibers and GRIN lenses in FC and SC standard ferrules, and verified the connection efficiency. As a result, a connection efficiency of 70% or higher was obtained for wavelengths of 445 nm, 515 nm, and 638 nm upon facing a pair of ferrules with the same specifications towards each other inside corresponding FC and SC standard split sleeves with a gap of between 0.5 mm and 2 mm, depending on the specifications. The reproducibility of the gap width at that time was 0.01 mm or less after 1000 or more attachments and detachments. In this way, the reproducibility for an approximately 1 mm gap formed between two ferrules was 10 µm or less, and the change in connection efficiency could be reduced.

According to this embodiment, the ferrules 27 and 37 are loosely fit in the corresponding connectors 20 and 30 to be displaceable within a predetermined range in the direction along the optical axis of the optical fibers. Therefore, when inserted in the split sleeve 15, the ferrules 27 and 37 are always positioned at the position furthest removed in the insertion direction relative to the connectors 20 and 30 within a predetermined range. Hence, an optical fiber connection mechanism and an optical fiber connection method for which the width of the gap between the ferrules 27 and 37 does not change even upon repeated attachment and detachment can be provided.

If the two ferrules 27 and 37 are slid in the optical axis direction in a state without play in the direction orthogonal to the optical axis, then fitting the ferrules 27 and 37 into the split sleeve 15 by a spring force leads to the problem of poor learning of the ferrules 27 and 37 with respect to the split sleeve 15. In this context, "learning" refers to consistently facing the direction towards the split sleeve 15. In other words, the "learning" in this case indicates the degree to which the central axis of the ferrules 27 and 37 is aligned with the direction towards the central axis of the split sleeve 15. According to the present disclosure, the ferrules 27 and 37 are loosely fit in the corresponding connectors 20 and 30 to be displaceable within a predetermined range in an in-plane direction orthogonal to the optical axis of the single-mode optical fibers 25 and 35, and no spring is provided. Therefore, since there is no large force pushing the ferrules 27 and 37 when the connectors 20 and 30 are connected, the ferrules 27 and 37 are easily aligned in the direction towards the split sleeve 15 without being inclined. The learning of the ferrules 27 and 37 with respect to the split sleeve 15 is therefore good, and the change in connection efficiency due to repeated attachment and detachment is reduced while maintaining a high connection efficiency.

The connecting portions between the connector housings 21 and 31 and the optical fiber cables 24 and 34 are partially fixed to each other so that the ferrules 27 and 37 do not move within the cavities 23 and 33 and the split sleeve 15 even if an external force is applied to the optical fiber cables 24 and 34. On the other hand, while not illustrated, the optical fiber cables 24 and 34 have slack so that the ferrules 27 and 37 are displaceable within the connectors 20 and 30.

Embodiment 2

Figure 3:
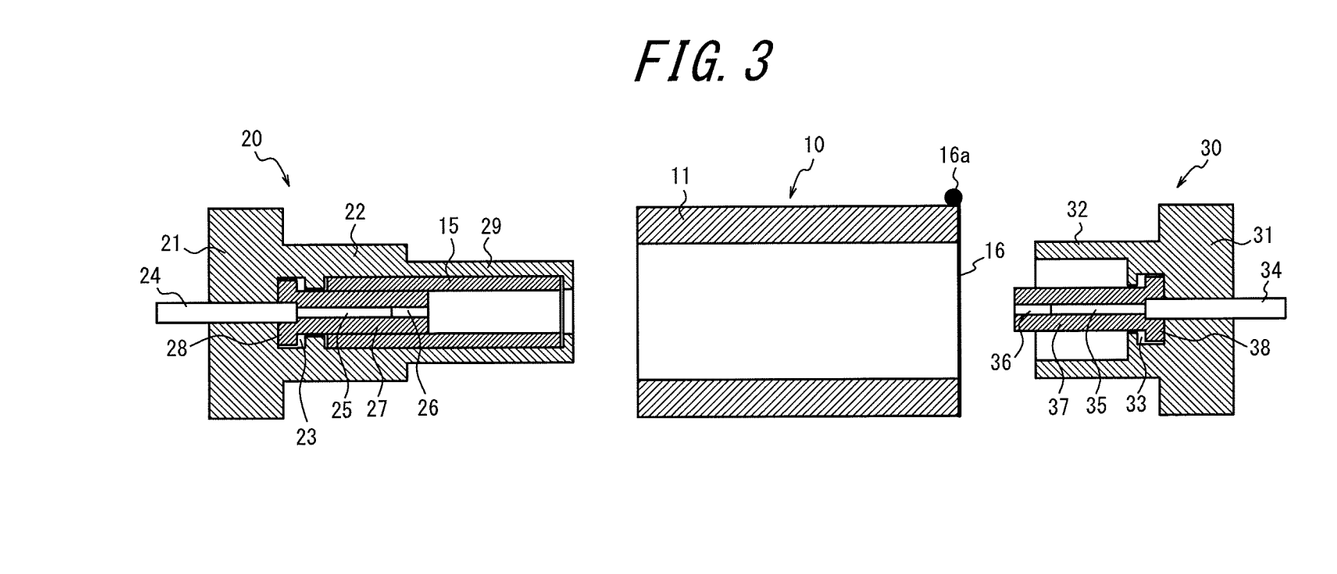
FIG. 3 is a longitudinal sectional view of an adapter and connectors according to Embodiment 2.
Figure 4:
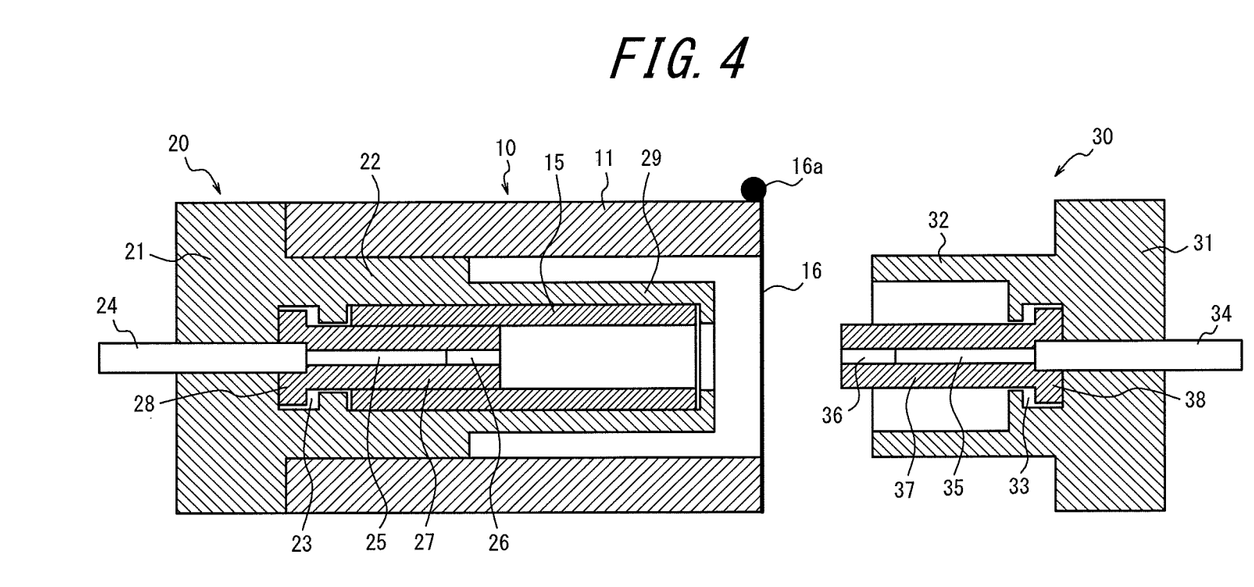
FIG. 4 is a longitudinal sectional view of the adapter in FIG. 3 with one of the connectors coupled thereto.
Figure 5:
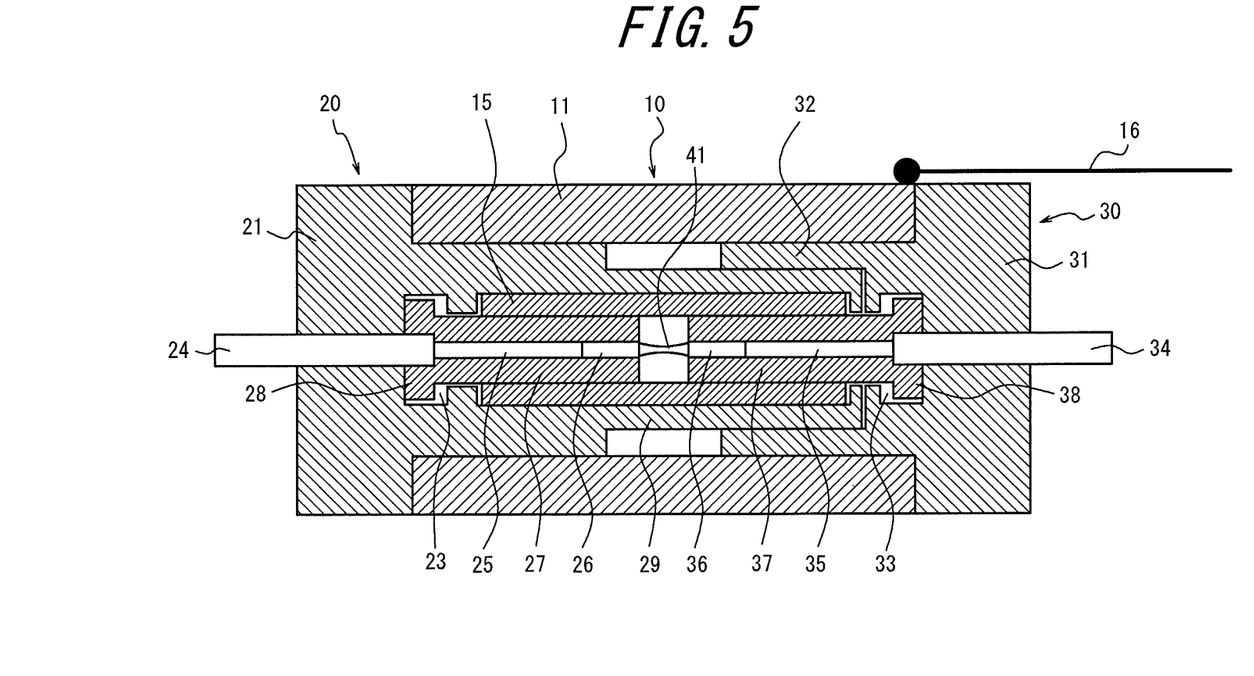
FIG. 5 is a longitudinal sectional view of the adapter in FIG. 4 with the other connector also coupled thereto.

The connection mechanism according to Embodiment 2 is for connecting single-mode optical fibers 25 and 35 in an endoscope apparatus between the inside of a housing and a scope. FIG. 3 is a longitudinal sectional view of an adapter 10 and connectors 20 and 30 according to Embodiment 2. In this case, the adapter 10 is fixed to the side face of a non-illustrated housing, and the connector 20 is disposed inside the housing. The connector 30 is the scope-side connector. The connector 20 is normally connected to the adapter 10, whereas the scope-side connector 30 is repeatedly detached, since the scope is cleaned upon each use. FIG. 4 is a longitudinal sectional view of the adapter 10 in FIG. 3 with the housing-side connector 20 coupled thereto. FIG. 5 is a longitudinal sectional view of the adapter 10 in FIG. 4 with the scope-side connector 30 further coupled thereto.

The adapter 10 and the connectors 20 and 30 of this embodiment share a number of points in common with the adapter 10 and the connectors 20 and 30 of Embodiment 1. The following describes the differences from Embodiment 1.

First, the adapter 10 has an outer cylindrical portion 11 and an opening/closing shutter 16 (door) and includes neither an inner cylindrical portion nor a split sleeve. The opening/closing shutter 16 is connected to the outer cylindrical portion 11 via a hinge 16a and is forced in the closing direction in a state in which the connector 30 is not connected. On the other hand, in the connector 20, a split sleeve holder 29 projects further forward from the cylindrical portion 22. A split sleeve 15 is disposed in the split sleeve holder 29 so as to have play in the longitudinal and radial directions. In other words, the split sleeve 15 is integrated with the housing-side connector 20. A ferrule 27 of the connector 20 is fit into the split sleeve 15 in advance. An opening through which the ferrule 37 from the connector 30 passes is provided at the tip of the split sleeve holder 29. Since the remaining configuration is similar to Embodiment 1, identical or corresponding constituent elements are labeled with the same reference signs, and a description thereof is omitted.

With the above-described configuration, the connection mechanism of this embodiment achieves the same effects as those of Embodiment 1. Furthermore, when the endoscope is not in use, the adapter 10 and the connector 20 are connected, whereas the connector 30 is not connected, as illustrated in FIG. 4. At this time, the opening/closing shutter 16 is closed, thereby preventing dust and the like from outside the housing from entering into the adapter 10. While not illustrated, a cap that covers the end face of the ferrule 37 can be made mountable onto the scope-side connector 30 to prevent the end face of the ferrule 37 from becoming dirty when the scope is cleaned.

Embodiment 3

Figure 6:
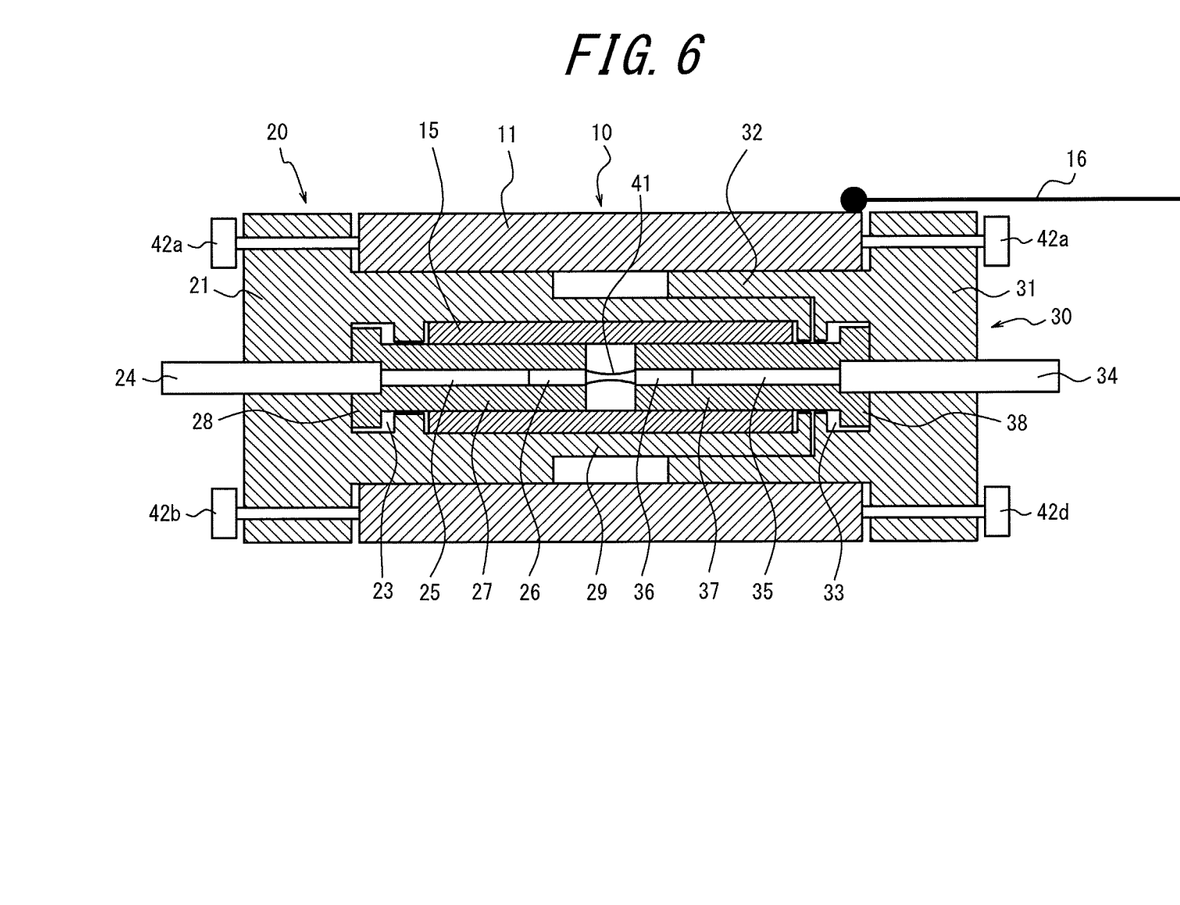
FIG. 6 is a longitudinal sectional view of an adapter and connectors according to Embodiment 3.

FIG. 6 is a longitudinal sectional view of an adapter 10 and connectors 20 and 30 according to Embodiment 3. The connectors 20, 30 of this embodiment are provided with adjustment screws 42a to 42d (adjustment mechanism) that contact the adapter 10 to form a contact surface and are capable of adjusting the width of the gap. The adjustment screws 42a to 42d can set the width of the gap by adjusting the projection length of the screws. The remaining configuration is similar to that of Embodiment 2.

According to this embodiment, the optimal width for the gap can be set using the adjustment screws 42a to 42d, thus yielding a high connection efficiency. Alternatively, the gap can be adjusted to yield a desired connection efficiency. The adjustment mechanism for adjusting the width of the gap is not limited to adjustment screws. For example, the width of the gap may also be adjusted by inserting rings of a particular width at the connection surface between the connectors 20 and 30 and the adapter 10.

Embodiment 4

Figure 7:
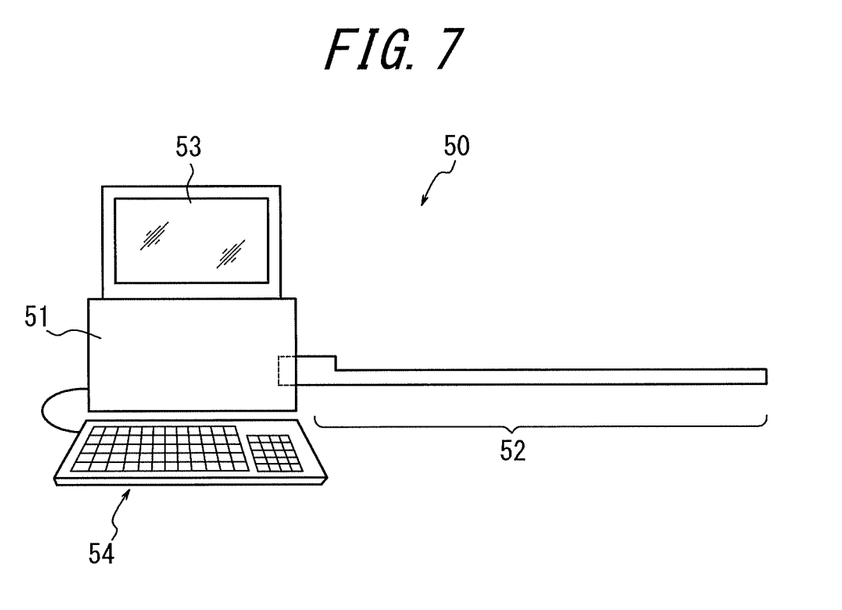
FIG. 7 is an external view schematically illustrating an endoscope apparatus that incorporates the adapter according to Embodiment 4.

FIG. 7 is an external view schematically illustrating an endoscope apparatus 50 that incorporates the adapter 10 according to Embodiment 4. The endoscope apparatus 50 is configured to include an endoscope body 51 mounted on a dedicated rack or the like contained in a regular housing and a scope 52 detachably connected to the endoscope body 51. The endoscope body 51 includes a light source and is also the portion that controls the system overall and that generates and processes images. A dedicated monitor for observation 53 and a setting input interface apparatus 54 for setting observation conditions and the like are connected to the endoscope body 51. The connection mechanism according to this embodiment is used for connection between an optical fiber cable 24 in the endoscope body 51 and an optical fiber cable 34 in the scope 52.

Figure 8:
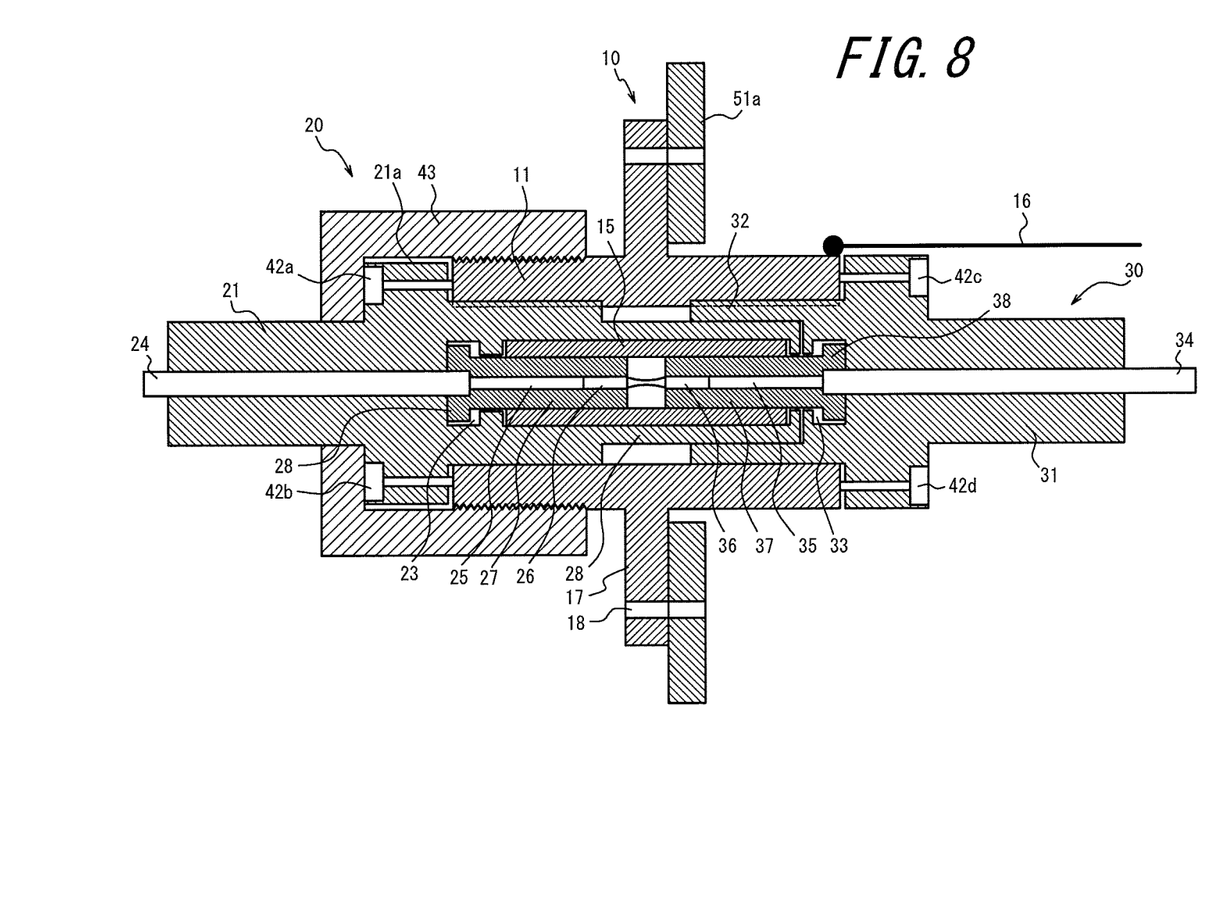
FIG. 8 is a longitudinal sectional view of an adapter and connectors according to Embodiment 4 in a coupled state.
Figure 9A:
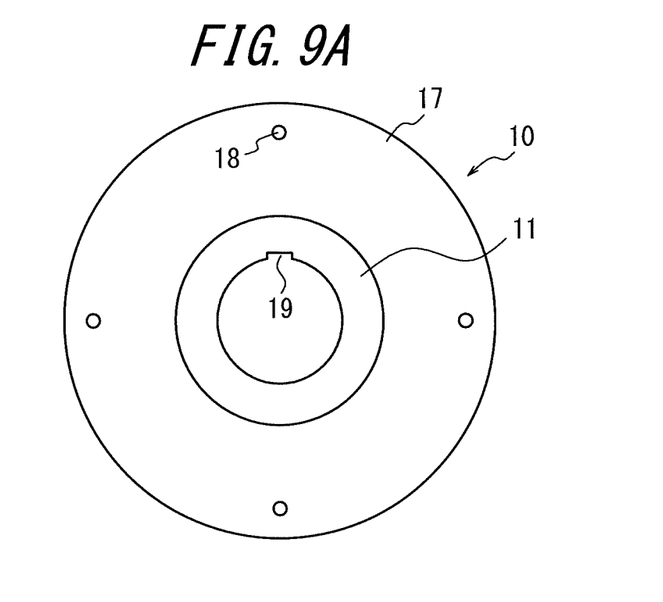
FIG. 9A is a front view of the adapter in FIG. 8.
Figure 9B:
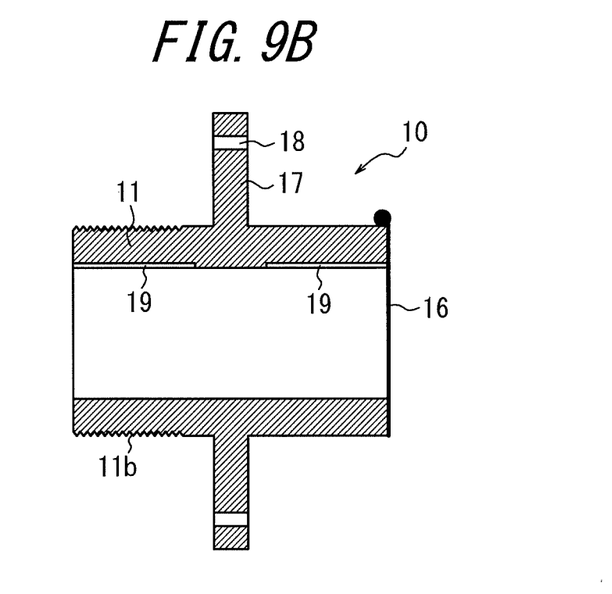
FIG. 9B is a longitudinal sectional view of the adapter in FIG. 8.
Figure 10A:
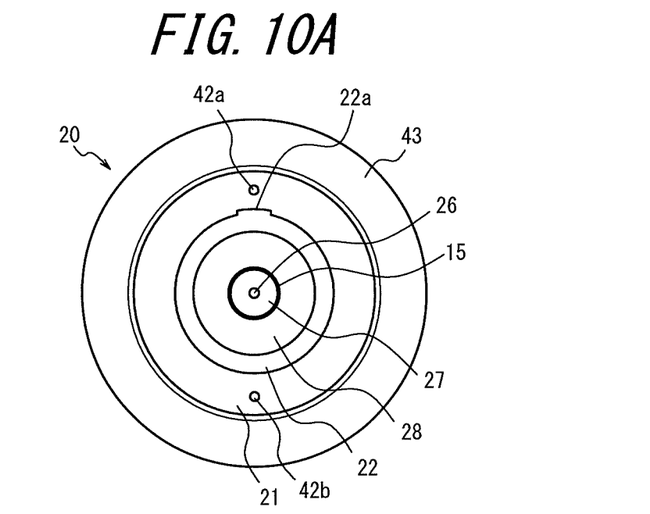
FIG. 10A is a front view of one of the connectors in FIG. 8.
Figure 10B:
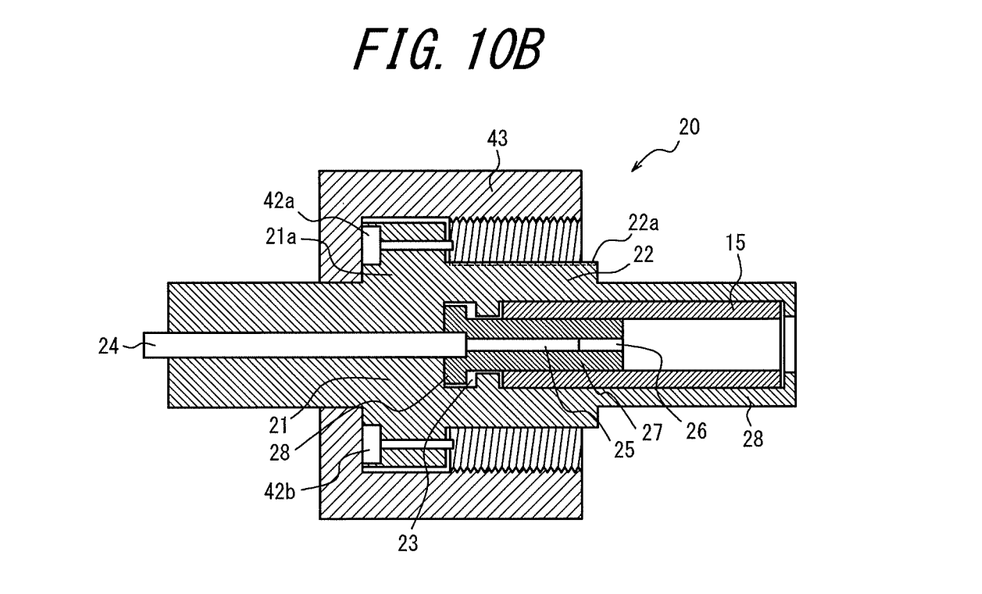
FIG. 10B is a longitudinal sectional view of one of the connectors in FIG. 8.
Figure 11A:
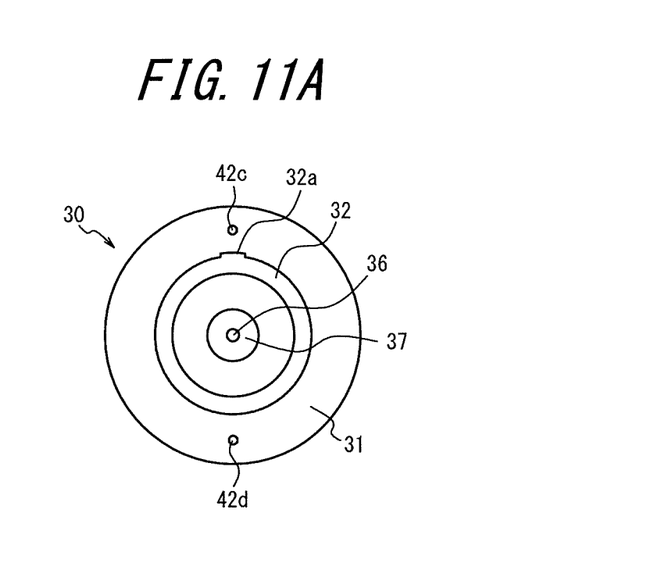
FIG. 11A is a front view of the other connector in FIG. 8.
Figure 11B:
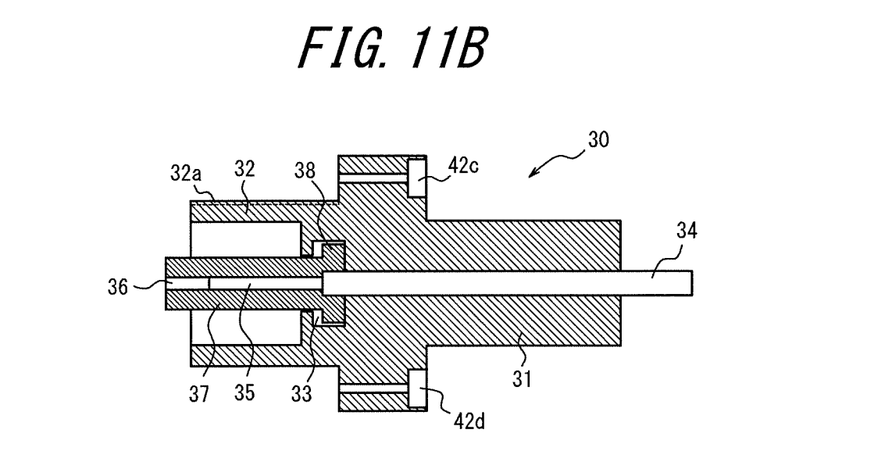
FIG. 11B is a longitudinal sectional view of the other connector in FIG. 8.

FIG. 8 is a longitudinal sectional view of an adapter 10 and connectors 20 and 30 according to Embodiment 4 in a coupled state. FIGS. 9A and 9B are respectively a front view and a longitudinal sectional view of the adapter 10 in FIG. 8. FIGS. 10A and 10B are respectively a front view and a longitudinal sectional view of the connector 20 in FIG. 8. Furthermore, FIGS. 11A and 11B are respectively a front view and a longitudinal sectional view of the connector 30 in FIG. 8. The adapter 10 and connectors 20 and 30 of this embodiment are similar in configuration to Embodiment 3. Therefore, the differences are described below.

First, as illustrated in FIG. 9A, the adapter 10 has a flange 17 for coupling to a housing 51a of the endoscope body 51. On the flange 17, a plurality of through holes 18 for housing fixing are provided in order to fix the flange 17 to the housing 51a by screwing. Furthermore, on the inner circumferential surface of the outer cylindrical portion 11, recesses extending in the direction along the central axis of the outer cylindrical portion 11 are provided as positioning guides 19. As illustrated in FIG. 9B, a screw thread 11b for fixing the connector 20 is formed on the outer circumferential surface of the outer cylindrical portion 11 towards the inside of the housing 51a. Furthermore, the adapter 10 is formed by a magnetic material.

As illustrated in FIG. 10A and FIG. 10B, the connector housing 21 on the housing-side connector 20 includes a flange 21a expanded in the radial direction. Furthermore, in the connector 20, a nut 43 that screws onto the screw thread 11b of the adapter 10 is provided from the back surface of the flange 21a of the connector housing 21 to the periphery of a cylindrical portion 22 of the connector housing 21. Also, a convexity that fits into the positioning guide 19 of the adapter 10 is formed on a portion of the periphery of the cylindrical portion 22 as a positioning key 22a. A recess that accommodates the head of the adjustment screws 42a and 42b is provided on the connector housing 21 so that adjustment screws 42a and 42b do not bump into the nut 43.

As illustrated in FIG. 11A and FIG. 11B, a similar positioning key 32a is also formed on the periphery of a cylindrical portion 32 of the scope 52-side connector 30. Furthermore, the connector housing 31 is formed by a magnet. Since the remaining configuration is similar to Embodiment 3, identical or corresponding constituent elements are labeled with the same reference signs, and a description thereof is omitted.

With the above-described configuration, the adapter 10 is fixed to the housing 51a of the endoscope body 51 by being screwed thereto. The connector 20 inside the housing 51a determines the rotation direction so that the positioning key 22a fits into the positioning guide 19 of the adapter 10. By rotating the nut 43 relative to the adapter 10, the flange 21a of the connector housing 21 is pressed by the nut 43 in a state in which rotation of the connector housing 21 is restricted, and the connector 20 advances towards the adapter 10. As a result, the connector 20 is fixed at a position where the tips of the adjustment screws 42a and 42b abut the adapter 10. At this time, the ferrule 27 is also pressed by the connector housing 21 and advances.

On the other hand, when connecting the scope 52-side connector 30, the opening/closing shutter 16 is opened, the rotation direction is determined so that the positioning key 32a fits into the positioning guide 19 of the adapter 10, and the ferrule 37 is fit into the split sleeve 15. The connector 30 advances until the tips of the adjustment screws 42c and 42d abut the adapter 10. At this time, rotation of the connector housing 31 is restricted by the positioning guide 19. At the same time, the ferrule 37 is also pressed by the connector housing 31 and advances. Since the connector housing 31 is formed by a magnet, the connector housing 31 is fixed by a magnetic force to the adapter 10 that is formed by a magnetic material.

As described above, according to this embodiment, like the connection mechanism of Embodiment 1, the width of the gap between the ferrules 27 and 37 does not change even upon repeated attachment and detachment, and a stable, high connection efficiency is obtained. Furthermore, rotation of the ferrules 27 and 37 is restricted during connection, thus increasing stability and yielding a connection with high reproducibility. The housing 51a-side connector 20 is continuously fixed by the nut 43, and the scope 52-side connector 30 is fixed by a magnetic force so as to be easily detachable. Therefore, this configuration facilitates detachment when cleaning the scope 52 and is suitable for connection of a single-mode optical fiber in the endoscope apparatus 50.

The present disclosure is not limited to the above embodiments, and a variety of changes and modifications may be made. For example, the shape of the adapter and connectors is not limited to a rotationally symmetric shape and may be any of a variety of shapes. The shape of the adapter and connectors may, for example, have a rectangular cross-section in the optical axis direction. Alternatively, the connectors and adapter may be configured by combining a plurality of the connection mechanisms of the present disclosure to connect a plurality of pairs of single-mode optical fibers together simultaneously. Latching of the adapter and connectors is not limited to a method based on screwing or magnets. Rather, a variety of methods may be adopted. For example, a projection for latching may be provided on the connector housing, and the projection may be fit into a recess on the adapter. Furthermore, the tubular member is not limited to a split sleeve, and a sleeve without a split may also be used. Also, the openable and closable door is not limited to one plate shaped member joined to the adapter by a hinge. Instead, a combination of a plurality of plate shaped members may be used.

The invention claimed is:

1. An optical fiber connection mechanism comprising:
a pair of connecting bodies and a tubular member that are used in an endoscope; wherein
the connecting bodies comprise respective ferrules, an end of an optical fiber and a collimator lens is mounted in each ferrule, the collimator lens is disposed at a tip of the optical fiber, and when the respective ferrules of the connecting bodies are inserted into ends of the tubular member, the collimator lenses face each other with a gap therebetween and the optical fibers are optically connected to each other; and
each ferrule is fit in the corresponding connecting body so as to be displaceable within a predetermined range in an in-plane direction orthogonal to an optical axis of the optical fiber.

2. The optical fiber connection mechanism of claim 1, wherein the optical fiber is a single-mode optical fiber.

3. An optical fiber connection mechanism comprising:
a pair of connecting bodies and a tubular member that are used in an endoscope; wherein
the connecting bodies comprise respective ferrules, an end of an optical fiber and a collimator lens is mounted in each ferrule, the collimator lens is disposed at a tip of the optical fiber, and when the respective ferrules of the connecting bodies are inserted into ends of the tubular member, the collimator lenses face each other with a gap therebetween and the optical fibers are optically connected to each other;
each ferrule is fit in the corresponding connecting body so as to be displaceable within a predetermined range in a direction along an optical axis of the optical fiber; and
an intermediate connecting body disposed between the pair of connecting bodies, wherein the intermediate connecting body has openings into which the connecting bodies are inserted, and a width of the gap is set by a connection surface between the intermediate connecting body and the connecting bodies.

4. The optical fiber connection mechanism of claim 3, wherein the tubular member is housed in one of the pair of connecting bodies.

5. The optical fiber connection mechanism of claim 3, wherein the intermediate connecting body comprises an openable and closable door on at least one of the openings into which the pair of connecting bodies is inserted.

6. The optical fiber connection mechanism of claim 3, wherein the connecting bodies comprise an adjustment mechanism that contacts the intermediate connecting body to form the connection surface and that is capable of adjusting the width of the gap.

7. The optical fiber connection mechanism of claim 3, wherein the optical fiber is a single-mode optical fiber.

8. An optical fiber connection method for connecting a pair of optical fibers for an endoscope, the connection method comprising:
preparing a pair of connecting bodies comprising respective ferrules, an end of an optical fiber and a collimator lens being mounted in each ferrule, the collimator lens being disposed at a tip of the optical fiber, and each ferrule being fit in the corresponding connecting body so as to be displaceable within a predetermined range in a direction along an optical axis of the optical fiber; and
optically connecting the pair of optical fibers by inserting the respective ferrules of the pair of connecting bodies into ends of a tubular member so that the collimator lenses face each other with a gap therebetween;
wherein the ferrules are fit in the corresponding connecting bodies so as to be displaceable within the predetermined range in an in-plane direction orthogonal to the optical axis of the optical fiber.

9. The optical fiber connection method of claim 8, wherein an intermediate connecting body is disposed between the pair of connecting bodies, the intermediate connecting body has openings into which the connecting bodies are inserted, and a width of the gap is set by causing the intermediate connecting body and the connecting bodies to come into contact.

10. The optical fiber connection method of claim 9, wherein the intermediate connecting body comprises an openable and closable door on at least one of the openings into which the pair of connecting bodies is inserted, the door is closed when one of the connecting bodies is not inserted into the opening provided with the door, and the door is opened when one of the connecting bodies is inserted into the opening provided with the door.

11. The optical fiber connection method of claim 8, wherein the optical fiber is a single-mode optical fiber.

* * * * *